US00PP10219P

United States Patent [19]

Pieters

[11] Patent Number: Plant 10,219

[45] Date of Patent: Jan. 27, 1998

[54] CHRYSANTHEMUM PLANT NAMED 'COBRA'

[76] Inventor: Dirk Pieters, Schierveldestraat 3A, Oosnieuwkerke, 8840 Staden, Belgium

[21] Appl. No.: 755,663

[22] Filed: Nov. 25, 1996

[51] Int. Cl.[6] ..... A01H 5/00

[52] U.S. Cl. ..... Plt./82.3

[58] Field of Search ..... Plt./74.1, 82.3

*Primary Examiner*—Howard J. Locker

*Attorney, Agent, or Firm*—C. A. Whealy

[57] ABSTRACT

A distinct cultivar of Chrysanthemum plant named 'Cobra', characterized by its upright, mounded and freely branching growth habit; daisy-type inflorescences; tan-colored ray and yellow-colored disc florets; numerous inflorescences per plant; and good garden performance.

2 Drawing Sheets

The present invention relates to a new and distinct cultivar of garden Chrysanthemum plant, botanically known as *Dendranthema grandiflora* and referred to by the cultivar name Cobra.

The new cultivar is a product of a planned breeding program conducted by the inventor in Staden, Belgium. The objective of the breeding program was to create new garden Chrysanthemum cultivars that are freely branching and have numerous and long-lasting inflorescences.

The new cultivar originated from a cross made by the inventor of the nonpatented cultivar Oberix as the female, or seed, parent with the nonpatented cultivar Rosso Brons as the male, or pollen, parent.

The new Chrysanthemum was discovered and selected by the inventor as a flowering plant within the progeny of the stated cross in a controlled environment in Staden, Belgium.

Asexual reproduction of the new cultivar by terminal cuttings taken at Staden, Belgium, has shown that the unique features of this new Chrysanthemum are stable and reproduced true to type in successive generations.

The following traits have been repeatedly observed and are determined to be the unique characteristics of 'Cobra'. These characteristics in combination distinguish 'Cobra' as a new and distinct cultivar:

1. Upright, mounded and freely branching growth habit, relatively vigorous.
2. Daisy-type inflorescences.
3. Tan-colored ray and yellow-colored disc florets.
4. Numerous inflorescences per plant.
5. Good garden performance.

The cultivar Cobra has not been observed under all possible environmental conditions. The phenotype may vary somewhat with variations in environment such as temperature, daylength and light intensity, without, however, any variance in genotype.

In side-by-side comparisons in Staden, Belgium, under commercial practice, plants of the new Chrysanthemum differ from plants of the female parent, the cultivar Oberix in ray floret color, inflorescence form and vigor. In the same comparisons, plants of the new Chrysanthemum differ from the male parent, the cultivar Rosso Brons, in ray floret color, foliage color, vigor, and inflorescence size.

The accompanying colored photographs illustrate the overall appearance of the new cultivar, showing the colors as true as it is reasonably possible to obtain in colored reproductions of this type.

The first photograph comprises a side perspective view of a typical flowering 16.5-cm container of 'Cobra' with five cuttings in the container.

The second photograph comprises a close-up view of typical inflorescences of the new Chrysanthemum. Foliage and floret colors in the photographs may appear different from the actual colors due to light reflectance.

In the following description, color references are made to The Royal Horticultural Society Colour Chart except where general terms of ordinary dictionary significance are used. The following observations and measurements describe plants grown in Oxnard, Calif., under commercial practice in a glass-covered greenhouse with night temperatures ranging between 14 and 20C., day temperatures ranging between 20 and 30C., and average light levels of 5,000 to 6,000 footcandles.

After sticking unrooted cuttings of the new cultivar, plants received 4 weeks of long day/short nights followed by short day/long nights until flowering. Measurements and numerical values represent ranges or averages for six typical flowering plants.

Botanical classification: *Dendranthema grandiflora* cultivar Cobra.

Commercial classification: Garden chrysanthemum.

Parentage:

*Female, or seed, parent.*—*Dendranthema grandiflora* cultivar Oberix (not patented).

*Male, or pollen, parent.*—*Dendrathema grandiflora* cultivar Rosso Brons (not patented).

Propagation:

*Type.*—Terminal tip cuttings.

*Time to rooting.*—10 to 12 days with soil temperatures of 20C.

*Rooting habit.*—Fine, fibrous and well-branched.

Plant description:

*Appearance.*—Perennial herbaceous garden plant. Upright with mounded inflorescence display. Vigorous and freely branching.

*Plant height.*—About 26 cm.

*Lateral branch length.*—About 18 to 20 cm.

*Quantity of lateral branches after removal of apical meristem.*—About 5 to 6.

*Stem color.*—147C.

*Foliage description.*—Number of leaves per plant: About 75 to 108. Number of leaves per lateral branch: About 15 to 18. Leaf arrangement: Alternate. Leaf size, fully expanded: Length: About 6 to 7 cm. Width: About 4 to 4.5 cm. Leaf apex: Mucronate. Leaf base: Attenuate. Leaf margin: Palmately lobed. Leaf texture: Fleshy. Abaxial and adaxial surfaces pubescent, smooth and dull. Veins prominent on adaxial surface. Petiole length: About 1.5 to 2 cm. Color: Young foliage adaxial surface: 147A. Young foliage abaxial surface: 147B. Fully expanded foliage adaxial surface: 147A. Fully expanded foliage abaxial surface: 147B. Venation abaxial surface: 147C. Venation adaxial surface: 147C. Petiole: 147B.

Inflorescence description:

*Appearance.*—Daisy-type inflorescence form. Inflorescences borne on terminals above foliage, arising from leaf axils. Disc and ray florets arranged acropetally on a flat capitulum.

*Flowering response.*—Under natural conditions, plants flower in the autumn. Inflorescence initiation and development can be induced under short day/long night conditions (at least 13.5 hours of darkness). Plants exposed to 3 or 4 weeks of long day/short night conditions after sticking followed by photoinductive short day/long night conditions, flower about 56 days later. Inflorescences maintain good substance for 3 weeks under bright natural daylight.

*Quantity of inflorescences.*—About 20 to 25 inflorescences per flowering stem.

*Inflorescence size.*—Diameter: About 4.5 to 5.5 cm. Depth (height): About 1.5 to 2 cm. Diameter of disc: About 1 cm.

*Opening inflorescences.*—Bud shape: Spherical becoming ovoid. Bud size: Length: About 1.25 to 1.5 cm. Width: About 1.25 cm. Bud color: 172B.

*Ray florets.*—Shape: Spatulate. Size: Length: About 2:5 to 2.75 cm. Width: About 5 to 10 mm. Apex: Variable, can be obtuse, rounded, acuminate, emarginate, mucronate or retuse. Base: Attenuate. Margin: Entire, wavy. Texture: Satiny, soft, smooth and glabrous. Number of ray florets per inflorescence: About 50 to 55. Color: When opening, adaxial surface: 167C. When opening, abaxial surface: 163C. Mature, adaxial surface: 163C. Mature, abaxial surface: 163D. Fading to, adaxial surface: 162C with hints of 37C. Fading to, abaxial surface: 11C with hints of 37D. After senescence: 162C with blotches of 37C.

*Disc florets.*—Shape: Tubular. Size: Length: About 8 mm. Width: About 1 mm. Number of disc florets per inflorescence: About 125. Color: Immature: 14B. Mature: 14A.

*Peduncle.*—Aspect: Strong, rigid and erect. Length: First peduncle: About 3 to 3.5 cm. Fourth peduncle: About 6 to 6.5 cm. Texture: Pubescent. Color: 147C/147D.

*Sepals.*—Shape: Linear. Apex: Acute. Margin: Entire. Texture: Adaxial surface, smooth and shiny; abaxial surface, pubescent. Quantity: About 24. Color: Adaxial surface: 146A and lighter. Abaxial surface: Close to 147A.

*Reproductive organs.*—Androecium: Only present on disc florets. Anther size: About 5 mm. Anther color: 14B. Pollen, amount: Moderate to low. Pollen color: 14B. Gynoecium: Present on both ray and disc florets. Stigma color: 14A. Style length: About 6 mm. Style color: 14C.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Cobra', as illustrated and described.

* * * * *

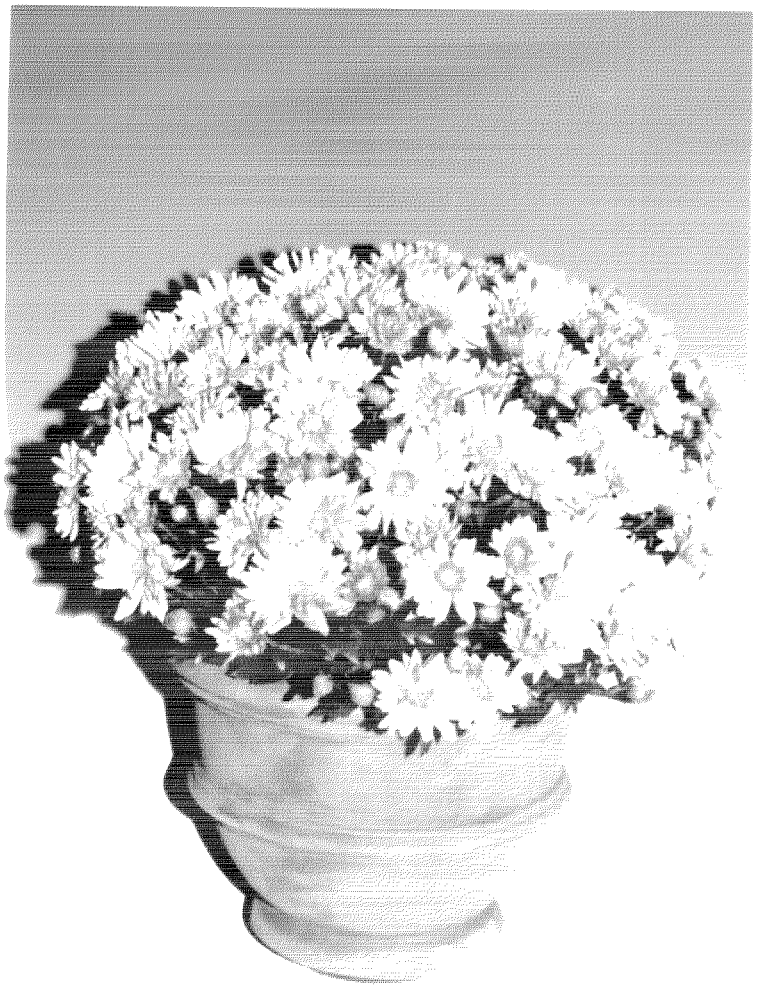

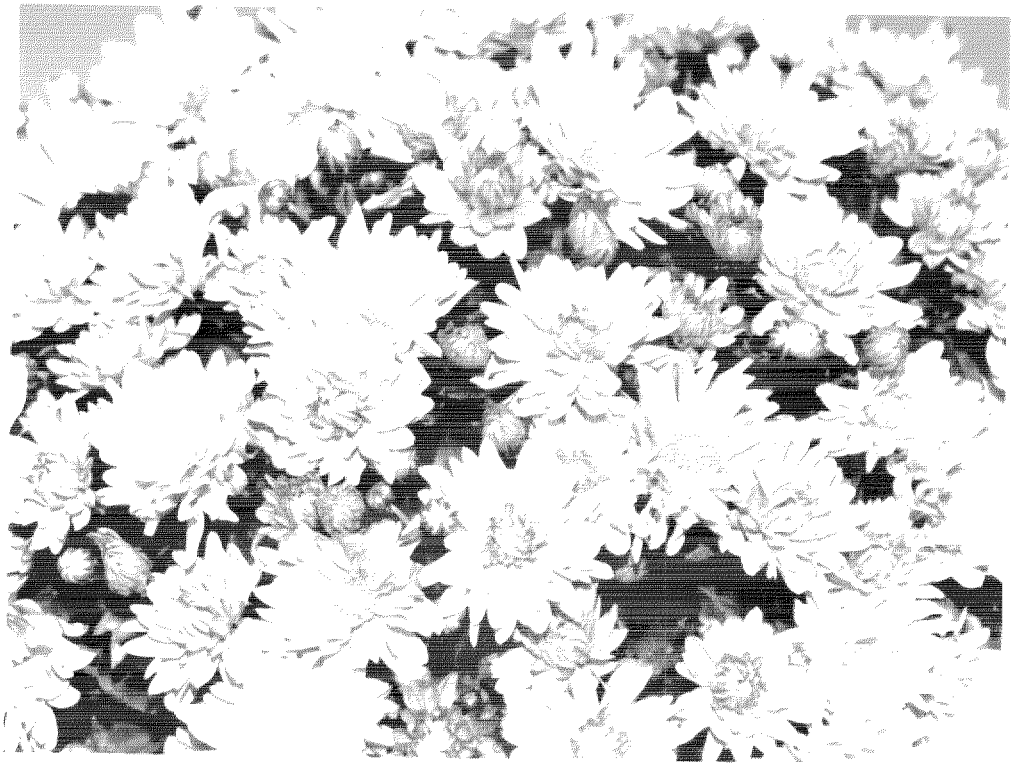

UNITED STATES PATENT AND TRADEMARK OFFICE

CERTIFICATE OF CORRECTION

PATENT NO. : Plant 10,219
DATED : January 27, 1998
INVENTOR(S) : Dirk Pieters

It is certified that error appears in the above-indentified patent and that said Letters Patent is hereby corrected as shown below:

Column 2, line 48, change "adaxial surface. Petiole" to
-- abaxial surface. Petiole --.
Column 3, line 27, change "About 2:5" to -- About 2.5 --.

Signed and Sealed this

Twenty-sixth Day of January, 1999

*Attest:*

*Attesting Officer*

*Acting Commissioner of Patents and Trademarks*